United States Patent [19]

Graf et al.

[11] Patent Number: 4,801,592
[45] Date of Patent: Jan. 31, 1989

[54] SUBSTITUTED 1,8-NAPHTHYRIDINE DERIVATIVES AND FUNGICIDES CONTAINING THEM

[75] Inventors: Hermann Graf, Mutterstadt; Lothar Franz, Ludwigshafen; Hubert Sauter, Mannheim; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 139,316

[22] Filed: Dec. 29, 1987

[30] Foreign Application Priority Data

Dec. 31, 1986 [DE] Fed. Rep. of Germany ....... 3644825

[51] Int. Cl.$^4$ .................. C07D 471/02; A01N 43/40
[52] U.S. Cl. ...................................... 514/300; 546/122
[58] Field of Search ......................... 546/122; 514/300

[56] References Cited

U.S. PATENT DOCUMENTS 4,031,103  6/1977  Williams et al. .................... 546/122

FOREIGN PATENT DOCUMENTS 1432967  4/1976  United Kingdom ................ 546/122
1496371 12/1977  United Kingdom ................ 546/122
2052481  1/1981  United Kingdom ................ 546/122

OTHER PUBLICATIONS

Domori et al., Chem. Abstracts, vol. 77 (1972) Item No. 140016z.
Czuba et al., Chem. Abstracts, vol. 85 (1976) Item No. 21166d.
Livi et al., Chem. Abstracts, vol. 86 (1977) Item No. 89704d.
Wozniak et al., Chem. Abstracts, vol. 87 (1977) Item No. 152164r.
Barlin et al., Chem. Abstracts, vol. 101 (1984) Item No. 130611q.
Chemical Week, Jun. 21, 1972, p. 46.
J. Chem. Soc., Perkin Transactions I, pp. 789–791.
J. Het. Chem., vol. 20, pp. 1053–1056 (1983).

*Primary Examiner*—Mary C. Lee
*Assistant Examiner*—Robert C. Whittenbaugh
*Attorney, Agent, or Firm*—Oblon, Fisher, Spivak, McClelland & Maier

[57] ABSTRACT

1,8-Naphthyridine derivatives of the formula

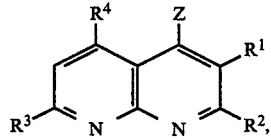

where $R^1$ is alkyl or alkoxyalkyl, $R^2$ and $R^3$ are alkyl, $R^4$ is hydrogen or—alkyl, Z is $NHR^5$ or $NH-NR^6R^7$, $R^5$ is hydrogen, allyl, benzyl or halobenzyl, and $R^6$ and $R^7$ are hydrogen, alkyl, formyl or $C_1-C_4$-alkyl—CO—, and fungicides containing these compounds.

5 Claims, No Drawings

SUBSTITUTED 1,8-NAPHTHYRIDINE DERIVATIVES AND FUNGICIDES CONTAINING THEM

The present invention relates to novel 1,8-naphthyridine derivatives having a fungicidal action, fungicides containing them, and processes for their manufacture.

The use of N-trichloromethylthiotetrahydrophthalimide as a fungicide has been disclosed (Chemical Week, June 12, 1972, p. 46). The compounds 2,7-dimethyl-4-hydroxy-1,8-naphthyridine (Hermecz et al, J. Chem. Soc., Perkin Trans. I, 1977, p. 789) and 2,7-dimethyl-4-chloro-1,8-naphthyridine (J. Het. Chem. 20, 1053–1056, 1983) have also been disclosed.

We have now found that 1,8-naphthyridine derivatives of the formula I

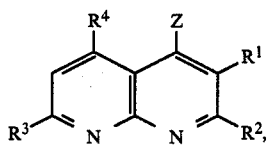

where $R^1$ is $C_4$–$C_{12}$-alkyl or $C_4$–$C_{12}$-alkoxy-$C_1$–$C_4$-alkyl, $R^2$ and $R^3$ are identical or different and each is $C_1$–$C_3$-alkyl, $R^4$ is hydrogen or $C_1$–$C_4$-alkyl, Z is $NHR^5$ or $NH$—$NR^6R^7$, $R^5$ is hydrogen, allyl, benzyl or halobenzyl, and $R^6$ and $R^7$ are identical or different and each is hydrogen, $C_1$–$C_4$-alkyl, formyl or $C_1$–$C_4$-alkyl-$CO$—, have a fungicidal action superior to that of prior art compounds.

Examples of $C_4$–$C_{12}$-alkyl are straight-chain or branched butyl, pentyl, hexyl, heptyl, octyl, nonyl, decyl, undecyl and dodecyl. Examples of $C_4$–$C_{12}$-alkoxy are straight-chain or branched butoxy, pentoxy, hexoxy, heptoxy, octyloxy, nonyloxy, decyloxy and dodecyloxy. Examples of $C_1$–$C_4$-alkyl are straight-chain or branched methyl, ethyl, propyl and butyl. Examples of halobenzyl are chlorobenzyl, dichlorobenzyl, bromobenzyl and dibromobenzyl. Examples of $C_1$–$C_4$-alkyl-CO are acetyl, propionyl and butyryl. Examples of halogen are chlorine and bromine.

The novel compounds may be prepared for instance as follows:

4-Hydroxy-1,8-naphthyridines of the formula Va, b,

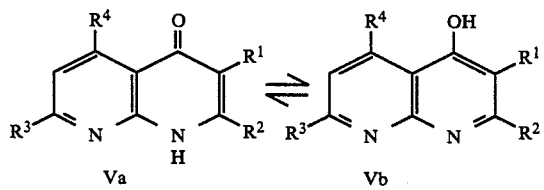

these compounds being predominantly in the Va form, are obtained by reacting a β-keto ester of the formula II

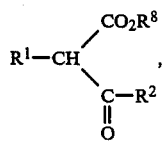

with a corresponding 2-aminopyridine of the formula III

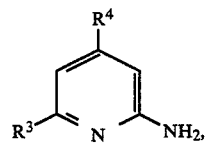

$R^8$ denoting $C_1$–$C_4$-alkyl and $R^1$ to $R^4$ having the above meanings, to give 4H-pyrido[1,2-a]pyrimidin-4-ones of the formula IV

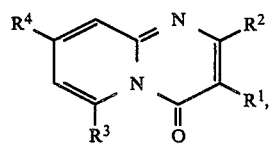

and rearranging these to 4-hydroxy-1,8-naphthyridines Va, b.

The 8-keto esters II may be prepared as described in Organic Synthesis Coll., Vol. 1, p. 248, or in DE-OS No. 3 227 388.

2-Aminopyridines of the formula III are listed in Beilstein, Handbuch der Organ. Chemie, Vol. E I 22, p. 633 et seq., Vol. E II 22, p. 342 et seq. and Vol. E III/IV 22, p. 4133 et seq.

The reaction of the β-keto esters II with the 2-aminopyridines III is advantageously carried out in solvents facilitating condensation. Suitable solvents are polyphosphoric acid or mixtures of polyphosphoric acid and phosphorus oxytrichloride or thionyl chloride, possibly diluted with an inert solvent such as toluene or xylene. Generally, the reaction temperature is from 80° to 200° C., and preferably from 100° to 150° C. The condensation products are isolated by evaporating off any inert solvents (toluene, xylene) which may still be present, neutralizing the reaction mixture by adding an aqueous solution of an alkali metal or alkaline earth metal hydroxide such as sodium, potassium or calcium hydroxide, washing the precipitate formed until it is phosphate-free, and carefully drying the residue.

If desired, this isolation may be followed by purification by crystallization from solvents such as pentane or ligroin.

The condensation products IV are rearranged to the 4-hydroxynaphthyridines Va, b in a high-boiling, inert solvent such as paraffin oil, diphenyl, diphenyl ether, a 1:1 mixture of diphenyl and diphenyl ether, liquid petrolatum, etc., at from 200° to 350° C., preferably 250° to 300° C. Stirring the cold reaction mixture into a solvent such as pentane, ligroin or cyclohexane precipitates the product, which can be separated by filtration. Further purification is usually not necessary.

The 4-hydroxynaphthyridines Va, b may be halogenated by reaction with phosphorus halides or sulfur halides, preferably phosphorus oxytrichloride or thionyl chloride. The halogenating agent may be reacted with the hydroxy compound in an excess as solvent or in (virtually) equimolar amounts in the presence of a solvent such as benzene, toluene, xylene; chlorobenzene, o-chlorobenzene, nitrobenzene; 1,1-dichloroethane, 1,2-dichloroethane, 1,1,1-trichloroethane or 1,1,2-trichloroethylene. A base, e.g., triethylamine or N,N-dimethylaniline, may be added in stoichiometric amounts or in an excess. The reaction temperature is from 50° to 200° C., preferably from 80° to 120° C. After excess halogenating agent or solvent has been evaporated off, the residue is treated with ice water, if desired with the addition of a water-immiscible solvent, and the base is, if desired, removed by extraction with an acid. The chlorination product thus obtained usually does not require any further purification.

The 4-hydroxynaphthyridines Va, b may also be converted to the corresponding 4-mercapto compounds VI (X=SH) by reaction with a sulfurization reagent such as hydrogen sulfide, phosphorus pentasulfide or 2,4-bis-(4-methoxyphenyl)-1,3-dithia-2,4-diphosphetan-2,4-disulfide (p-methoxyphenylthionophosphine sulfide) IX

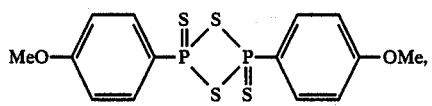

(see, for example, W. Walter et al, Synthesis 1979, 941). Examples of solvents which may be employed are pyridine, picolines, lutidines, collidines; 1,2-dimethoxyethane, tetrahydrofuran, 1,4-dioxane; hexamethylphosphoric triamide; tetramethylurea, N,N-dimethylethyleneurea and N,N-dimethylpropyleneurea.

The 4-mercapto compounds thus obtained may then be S-alkylated to give the corresponding 4-alkylthio compounds VI (X=S-alkyl). Examples of alkylating agents are alkyl halides such as methyl and ethyl chloride, methyl and ethyl bromide, alkyl tosylates and mesylates such as methyl p-tolylsulfonate and methyl methanesulfonate, and dialkyl sulfates such as dimethyl and diethyl sulfate. Alkylation may also be carried out with the addition of a base such as sodium or calcium carbonate, sodium or potassium hydroxide, and if desired in the presence of a solvent such as methanol, ethanol, butanol, acetone, 2-butanone, N,N-dimethylformamide and N,N-methylpyrrolidone, at from +20° to +150° C.

The 4-alkylthio compounds thus obtained may then be oxidized to give the corresponding 4-alkylsulfynyl and 4-alkylsulfonyl compounds VI (X=SO-alkyl or SO$_2$-alkyl), by allowing them to react with one or two equivalents of an oxidizing agent. Suitable oxidizing agents are hydrogen peroxide, peracetic acid, trifluoroperacetic acid, perbenzoic acid, m-chloroperbenzoic acid, tert-butyl hydroperoxide, N-methylmorpholine-N-oxide, potassium persulfate, potassium peroxodisulfate, and sodium perborate; suitable solvents are water, acetic acid, trifluoroacetic acid, methylene chloride, 1,2-dichloroethane, 1,1,1-trichloroethane and chlorobenzene. The reaction temperature is from 0° to +150° C., preferably from 40° to 80° C., with or without a catalyst.

The abovementioned 4-halo compounds VI (X=halogen), 4-mercapto compounds VI (X=SH), 4-alkylthio compounds VI (X=alkyl-S), 4-alkylsulfynyl compounds VI (X=alkyl-SO) and 4-alkylsulfonyl compounds VI (X=alkyl-SO$_2$) may be converted to the corresponding 4-hydrazino compounds VII by reaction with hydrazines such as hydrazine, methylhydrazine, 1,1-dimethylhydrazine, formylhydrazine and acetylhydrazine. Suitable solvents are ethers such as di-n-butyl ether, diethylene glycol dimethyl (and diethyl) ether, alcohols such as butanol, 2-ethylhexanol and ethylene glycol, and N,N-dimethylformamide, N-methylpyrrolidone and dimethyl sulfoxide. The reaction temperature is from +80° to +200° C.

By reaction with substituted or unsubstituted allyl or benzyl amines the same compounds as mentioned in the reaction with hydrazine may be converted into the corresponding 4-allylamino and 4-benzylamino compounds VIII, use being made either of two equivalents of an amine or one equivalent of an amine together with an auxiliary base such as triethylamine, diisopropylethylamine, 1,4-diazabicyclo[2.2.2]octane, 1,5-diazabicyclo[4.3.0]non-5-ene and 1,8-diazabicyclo[5.4.0]undec-7-ene. With regard to temperature and solvents, reference is made to the above section (reaction with hydrazines).

The abovementioned 4-hydrazino compounds VII and the 4-allylamino and 4-benzylamino compounds VIII may be converted with a suitable reducing agent into the corresponding 4-amino compounds I (Z=NH$_2$). Suitable reducing agents are hydrogen in the presence of a catalyst such as nickel, palladium and platinum, if desired dispersed on an inert carrier such as activated carbon, kieselguhr or aluminum oxide, or sodium dithionite (sodium hydrosulfite); suitable solvents are alcohols such as methanol, ethanol and butanol; carboxylic acids such as formic and acetic acid; ethers such as tetrahydrofuran and 1,4-dioxane, if desired in admixture with water, or—in the case of sodium dithionite—aqueous alkaline solutions such as sodium hydroxide and potassium hydroxide solutions, if desired with the addition of a solubilizer such as ethanol, 1,4-dioxane and ethylene glycol.

Compounds VI may also (if required, at superatmospheric pressure and elevated tmperatures) be reacted with ammonia or metal amides such as lithium, sodium and potassium amides to give the corresponding compounds I (Z=NH$_2$) direct. In the reaction with ammonia, pressures of from 20 to 200 bar (19.4 to 194 k Pa) and temperatures of from 80° to 100° C. are employed, ammonia being used in a 5- to 50-fold excess. The reaction is advantageously carried out in a solvent such as tetrahydrofuran, 1,4-dioxane, 1,2-dimethoxyethane and sulfolane (tetrahydrothiophene-1,1-dioxide). The reaction with metal amides may be carried out at atmospheric or superatmospheric pressure, with equivalent amounts or an excess of metal amide in the abovementioned solvents of from 50° to 250° C., if desired with the addition of a reaction accelerator such as 12-crown-4, 15-crown-5, 18-crown-6 and dibenzo-18-crown-6.

MANUFACTURING EXAMPLE

4-Amino-2,7-dimethyl-3-n-octyl-1,8-naphthyridine (a)

3,5-Dimethyl-2-n-octyl-4H-pyrido[1,2-a]-pyrimidin-4-one (Example 13A)

While stirring, 10.8 g (100 mmol) of 2-amino-6-methylpyridine is added to 100 g of polyphosphoric acid. This mixture is heated to 120° C. over a 2-hour period, 22.8 g (100 mmol) of methyl 2-n-octylacetoacetate being dripped in. The resultant mixture is stirred for 30 minutes, and is then allowed to cool. 100 ml of water is then introduced, and the reaction mixture is stirred overnight. A solution of 75 g of sodium hydroxide in 250 ml of water is added, while cooling, to the uniform solution which is formed and the mixture is stirred at room temperature (20° C.) until the formation of a yellow precipitate is over. This precipitate is filtered off, washed intensively with 1.5 liters of water, subjected to suction drying, and then carefully dried. Yield: 23.9 g (83%) of a uniform (according to thin-layer chromatography) powder of m.p. 42°–45° C. Dissolution in ligroin and reprecipitation gives virtually colorless crystals of m.p. 56°–58° C.

(b) 4-Hydroxy-2,7-dimethyl-3-n-octyl-1,8-naphthyridine (Example 13B)

250 ml of viscous paraffin oil is heated to 300° C., and 14.3 g (50.0 mmol) of the product from (a) is added in small portions. After a reaction period of 30 minutes the mixture is allowed to cool, 250 ml of ligroin is added, the resultant mixture is stirred for 1.5 hours and the precipitate which has formed is filtered off. After washing and drying there is obtained 5.72 g (40%) of a gray powder of m.p. 215°–216° C. According to infrared spectra, the compound is virtually completely in the 1H-4-keto form.

(c) 4-Chloro-2,7-dimethyl-3-n-octyl-1,8-naphthyridine (Example 13C)

58.0 g (203 mmol) of the product from (b) is refluxed for 18 hours in 400 ml of phosphorus oxytrichloride. After cooling, excess chlorinating agent is distilled off. The residue is dissolved in dichloromethane, and the solution is washed with dilute sodium bicarbonate solution and water, dried and concentrated. The residue is triturated with pentane. Yield: 42 g (68%), m.p. 68°–69° C., uniform according to thin-layer chromatography.

(d) 4-Hydrazino-2,7-dimethyl-3-n-octyl-1,8-naphthyridine (Example 13D)

43.0 g (141 mmol) of the product from (c) is refluxed for 12 hours in 400 ml of hydrazine hydrate. After cooling, the precipitated material is filtered off, dissolved in dichloromethane, washed three times with water, dried and concentrated. The residue is triturated with pentane, suction filtered and dried. Yield: 33.4 g (79%), m.p. 103°–104° C.

(e) 4-Amino-2,7-dimethyl-3-n-octyl-1,8-naphthyridine (Example 13E)

33.4 g (111 mmol) of the product from (d) is suspended in 600 ml of 10% strength aqueous sodium hydroxide solution. The mixture is heated to 65° C. and approx. 300 ml of ethanol is added until a clear solution is formed. The solution is allowed to cool to 45° C. before 19.7 g (113 mmol) of sodium dithionite is added. The mixture is subsequently refluxed for 12 hours. Upon cooling a precipitate forms which is suction filtered, washed with water and suction dried. The residue is treated with pentane, again suction filtered and dried. Yield: 23.8 g (75%), m.p. 176°–178° C.

The active ingredients for which physical data are given in the tables below were obtained by the above methods. Those without physical data may be readily obtained by changing the raw materials and adapting the manufacturing instructions accordingly; because of their structural similarity they can be expected to have a comparable action.

The abbreviations employed in the tables have the following meanings:

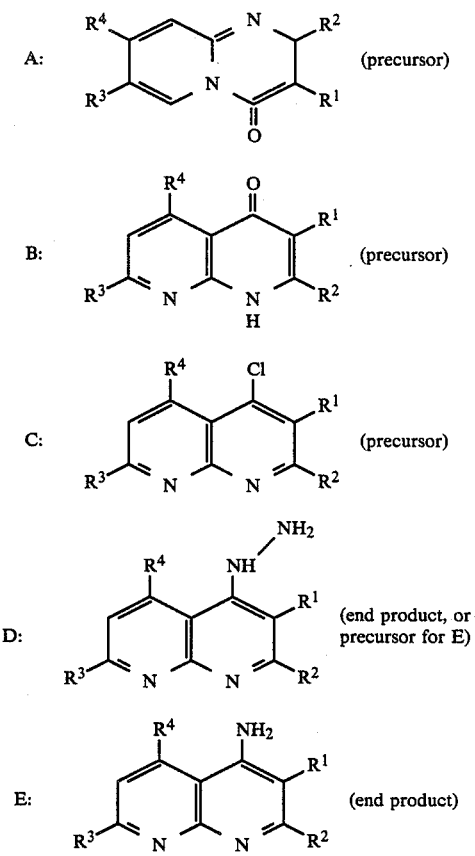

TABLE

| No. | R$^1$ | R$^2$ | R$^3$ | R$^4$ | A m.p. (°C.) | B m.p. (°C.) | C m.p. (°C.) | D m.p. (°C.) | E m.p. (°C.) |
|---|---|---|---|---|---|---|---|---|---|
| 1 | n-C$_4$H$_9$ | CH$_3$ | CH$_3$ | H | | | | | |
| 2 | n-C$_4$H$_9$ | CH$_3$ | CH$_3$ | CH$_3$ | | | | | |
| 3 | i-C$_4$H$_9$ | CH$_3$ | CH$_3$ | H | | | | | |
| 4 | i-C$_4$H$_9$ | CH$_3$ | CH$_3$ | CH$_3$ | | | | | |
| 5 | n-C$_5$H$_{11}$ | CH$_3$ | CH$_3$ | H | 54–55 | 217–218 | 84–85 | 157–158 | 207–208 |
| 6 | n-C$_5$H$_{11}$ | CH$_3$ | CH$_3$ | CH$_3$ | | | | | |
| 7 | i-C$_5$H$_{11}$ | CH$_3$ | CH$_3$ | H | | | | | |
| 8 | i-C$_5$H$_{11}$ | CH$_3$ | CH$_3$ | CH$_3$ | | | | | |
| 9 | n-C$_6$H$_{13}$ | CH$_3$ | CH$_3$ | H | 50–51 | 227–228 | 68–69 | 152–153 | 193–194 |
| 10 | n-C$_6$H$_{13}$ | CH$_3$ | CH$_3$ | CH$_3$ | | | | | |
| 11 | n-C$_7$H$_{15}$ | CH$_3$ | CH$_3$ | H | | | | | |
| 12 | n-C$_7$H$_{15}$ | CH$_3$ | CH$_3$ | CH$_3$ | | | | | |
| 13 | n-C$_8$H$_{17}$ | CH$_3$ | CH$_3$ | H | 56–58 | 215–216 | 68–69 | 103–104 | 176–178 |
| 14 | n-C$_8$H$_{17}$ | CH$_3$ | CH$_3$ | CH$_3$ | | | | | |
| 15 | n-C$_9$H$_{19}$ | CH$_3$ | CH$_3$ | H | | | | | |

TABLE-continued

| No. | R$^1$ | R$^2$ | R$^3$ | R$^4$ | A m.p. (°C.) | B m.p. (°C.) | C m.p. (°C.) | D m.p. (°C.) | E m.p. (°C.) |
|---|---|---|---|---|---|---|---|---|---|
| 16 | n-C$_9$H$_{19}$ | CH$_3$ | CH$_3$ | CH$_3$ | | | | | |
| 17 | n-C$_{10}$H$_{21}$ | CH$_3$ | CH$_3$ | H | | | | | |
| 18 | n-C$_{10}$H$_{21}$ | CH$_3$ | CH$_3$ | CH$_3$ | | | | | |
| 19 | n-C$_{11}$H$_{23}$ | CH$_3$ | CH$_3$ | CH$_3$ | | | | | |
| 20 | n-C$_{12}$H$_{25}$ | CH$_3$ | CH$_3$ | CH$_3$ | | | | | |
| 21 | (n-C$_3$H$_7$)(CH$_3$)CHCH$_2$ | CH$_3$ | CH$_3$ | H | | | | | |
| 22 | (n-C$_3$H$_7$)(CH$_3$)CHCH$_2$ | CH$_3$ | CH$_3$ | CH$_3$ | | | | | |
| 23 | (C$_2$H$_5$)(CH$_3$)CHCH$_2$ | CH$_3$ | CH$_3$ | H | | | | | |
| 24 | (C$_2$H$_5$)(CH$_3$)CHCH$_2$ | CH$_3$ | CH$_3$ | CH$_3$ | | | | | |
| 25 | (C$_2$H$_5$)$_2$CHCH$_2$ | CH$_3$ | CH$_3$ | H | | | | | |
| 26 | (C$_2$H$_5$)$_2$CHCH$_2$ | CH$_3$ | CH$_3$ | CH$_3$ | | | | | |
| 27 | (n-C$_4$H$_9$)(C$_2$H$_5$)CHCH$_2$ | CH$_3$ | CH$_3$ | H | | | | | |
| 28 | (n-C$_4$H$_9$)(C$_2$H$_5$)CHCH$_2$ | CH$_3$ | CH$_3$ | CH$_3$ | | | | | |
| 29 | t-C$_4$H$_9$CH$_2$(CH$_3$)CHCH$_2$ | CH$_3$ | CH$_3$ | H | | | | | |
| 30 | t-C$_4$H$_9$CH$_2$(CH$_3$)CHCH$_2$ | CH$_3$ | CH$_3$ | CH$_3$ | | | | | |
| 31 | t-C$_4$H$_9$CH$_2$(CH$_3$)CH(CH$_2$)$_2$ | CH$_3$ | CH$_3$ | H | oil | 204–207 | 79–82 | 100–104 | resin |
| 32 | t-C$_4$H$_9$CH$_2$(CH$_3$)CH(CH$_2$)$_2$ | CH$_3$ | CH$_3$ | CH$_3$ | | | | | |
| 33 | (n-C$_4$H$_9$)(C$_2$H$_5$)CH—CH$_2$<br>  \|<br>H$_2$C—CH(CH$_3$)—O | CH$_3$ | CH$_3$ | H | | | | | |
| 34 | (n-C$_4$H$_9$)(C$_2$H$_5$)CH—CH$_2$<br>  \|<br>CH$_2$—HC(CH$_3$)—O | CH$_3$ | CH$_3$ | CH$_3$ | | | | | |
| 35 | t-C$_4$H$_9$CH$_2$CH(CH$_3$)(CH$_2$)$_2$<br>  \|<br>CH$_2$—CH(CH$_3$)—O | CH$_3$ | CH$_3$ | H | | | | | |
| 36 | t-C$_4$H$_9$CH$_2$CH(CH$_3$)(CH$_2$)$_2$<br>  \|<br>CH$_2$—CH(CH$_3$)—O | CH$_3$ | CH$_3$ | CH$_3$ | | | | | |
| 37 | (C$_2$H$_5$)$_2$CHCH$_2$—O<br>            \|<br>    H$_2$C—CH(CH$_3$) | CH$_3$ | CH$_3$ | H | | | | | |
| 38 | (C$_2$H$_5$)$_2$CHCH$_2$—O<br>            \|<br>    H$_2$C—CH(CH$_3$) | CH$_3$ | CH$_3$ | CH$_3$ | | | | | |

The novel active ingredients have a strong fungitoxic action on phytopathogenic fungi, especially those from the Phycomycetes class. They are therefore suitable for combating from instance *Phytophthora infestans* in tomatoes and potatoes, *Phytophthora parasitica* in strawberries, *Phytophthora cactorum* in apples, *Pseudoperonospora cubensis* in cucumbers, *Pseudoperonospora humuli* in hops, *Peronospora destructor* in onions, *Peronospora sparsa* in roses, *Peronospora tabacina* in tobacco, *Plasmopara viticola* in grapes, Plasmopara halstedii in sunflowers, *Sclerospora macrospora* in Indian corn, *Bremia lactucae* in lettuce, *Mucor mucedo* in fruit, *Rhizopus nigricans* in beets, and *Erysyphe graminis* in cereals, *Uncinula necator* in grapes, *Podophaera leucotricha* in apples, and *Pyrenophora teres* in barley.

The active ingredients are well tolerated by plants. Some of them have curative properties, i.e., the agents may be applied after infection of the plants by the pathogen, and success is still ensured.

The fungicidal agents contain from 0.1 to 95, and preferably from 0.5 to 90, wt% of active ingredient. Application rates depend on the effect desired, and range from 0.1 to 5 kg/ha.

In these application forms, the agents according to the invention may also be present together with other active ingredients, for example herbicides, insecticides, growth regulators, and other fungicides, and may furthermore be mixed and applied together with fertilizers. Admixture with other fungicides frequently results in a greater fungicidal action spectrum. With some of these fungicidal mixtures, synergistic effects also occur, i.e., the fungicidal action of the combination is greater than the action of the individual components added together.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
znc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and
N,N'-polypropylenebis(thiocarbamoyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfonic acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(N-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboxamide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or water. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phospate, ammonium nitrate, and ureas, and vegetable products such as grain flours, bark meal, wood meal, and nutshell meal, cellulosic powders, etc.

Examples of formulations are given below.

I. 90 parts by weight of the compound of Example 9 is mixed with 10 parts by weight of N-methyl-alpha-pyrrolidone. A mixture is obtained which is suitable for application in the form of very fine drops.

II. 20 parts by weight of the compound of Example 13 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of the compound of Example 13 is dissolved in a mixture consisting of 30 parts by weight of cyclohexanone, 30 parts by weight of isobutanol, and 20 parts by weight of the adduct of 40 moles of ethylene oxide and 1 mole of castor oil. By pouring the solution into water and stirring it therein, an aqueous dispersion is obtained.

IV. 20 parts by weight of the compound of Example 9 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and stirring it therein, an aqueous dispersion is obtained.

V. 20 parts by weight of the compound of Example 13 is well mixed with 3 parts by weight of the sodium salt of diisobutylnaphthalene-alphasulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in water, a spray liquor is obtained.

VI. 5 parts by weight of the compound of Example 9 is intimately mixed with 95 parts by weight of particulate kaolin. A dust is obtained containing 5% by weight of the active ingredient.

VII. 30 parts by weight of the compound of Example 13 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 13 is intimately mixed with 30 parts of the sodium salt of a phenolsulfonic acid-urea-formaldehyde condensate, 2 parts of silica gel and 48 parts of water to give a stable aqueous dispersion.

IX. 20 parts of the compound of Example 9 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

For the following use examples, the prior art compounds N-trichloromethylthiotetrahydrophthalimide (A, Chem. Week, June 21, 1972, p. 46) and 2,7-dimethyl-4-hydroxy-1,8-naphthyridine (B, Hermecz et al, J. Chem. Soc., Perkin Trans. I, 1977, p. 789) were used for comparison purposes.

USE EXAMPLE 1

Action on *Phytophthora infestans* in tomatoes

Leaves of potted tomatoes of the "Große Fleischtomate" variety were sprayed with aqueous liquors containing (dry basis) 80 wt% of active ingredient and 20 wt% of emulsifier. 24 hours later, the leaves were infected with a zoospore suspension of the fungus *Phytophthora infestans*. The plants were then set up in water vapor-saturated chamber at from 16° to 18° C. The disease had spread to such an extent on the untreated (infected) control plants that the fungicidal action of the compounds was able to be assessed.

The results show that compound 13E, applied as a 0.025 wt% spray liquor, had a better fungicidal action (97%) than prior art active ingredient A (90%).

USE EXAMPLE 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. In accelerate and intensify the sporangiophore discharge, the plants were then again placed in the moist chamber for 16 hours. The extent of fungus attack was then assessed on the undersides of the leaves.

The results show that for example compounds 9E, 13D and 13E, applied as a 0.05% spray liquor, had a good fungicidal action (100%).

We claim:

1. A 1,8-naphthyridine derivative of the formula I

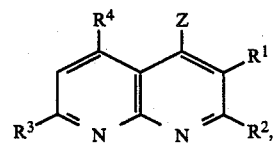

where $R^1$ is $C_4$–$C_{12}$-alkyl or $C_4$–$C_{12}$-alkoxy-$C_1$–$C_4$-alkyl, $R^2$ and $R^3$ are identical or different and each is $C_1$–$C_3$-alkyl, $R^4$ is hydrogen or $C_1$–$C_4$-alkyl, Z is $NHR^5$ or NH—NR⁶R⁷, $R^5$ is hydrogen, allyl, benzyl or halobenzyl, and $R^6$ and $R^7$ are identical or different and each is hydrogen, $C_1$–$C_4$-alkyl, formyl or $C_1$–$C_4$-alkyl-CO—.

2. A process for combating fungi wherein the fungi, or the materials, plants, soil or seed to be protected against fungus attack are treated with a fungicidally effective amount of a 1,8-naphthyridine derivative of the formula

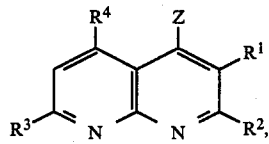

where $R^1$ is $C_4$–$C_{12}$-alkyl or $C_4$–$C_{12}$-alkoxy-$C_1$–$C_4$-alkyl, $R^2$ and $R^3$ are identical or different and each is $C_1$–$C_3$-alkyl, $R^4$ is hydrogen or $C_1$–$C_4$-alkyl, Z is NHR⁵ or NH—NR⁶R⁷, $R^5$ is hydrogen, allyl, benzyl or halobenzyl, and $R^6$ and $R^7$ are identical or different and each is hydrogen, $C_1$–$C_4$-alkyl, formyl or $C_1$–$C_4$-alkyl-CO—.

3. 4-Amino-2,7-dimethyl-3-n-octyl-1,8-naphthyridine.

4. 4-Amino-2,7-dimethyl-3-n-hexyl-1,8-naphthyridine.

5. A fungicidal composition having fungitoxic action on phytopathogenic fungi comprising a fungitoxically effective amount of a 1,8-naphthyridine derivative of formula I of claim 1 in an inert fungicidally acceptable carrier.

* * * * *